: US009044340B2

(12) United States Patent
Strøbech et al.

(10) Patent No.: US 9,044,340 B2
(45) Date of Patent: Jun. 2, 2015

(54) CUSTOMIZABLE COLLECTION DEVICE

(75) Inventors: Esben Strøbech, Hoersholm (DK); Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 110 days.

(21) Appl. No.: 13/695,064

(22) PCT Filed: Apr. 29, 2011

(86) PCT No.: PCT/DK2011/050146
§ 371 (c)(1),
(2), (4) Date: Dec. 12, 2012

(87) PCT Pub. No.: WO2011/134482
PCT Pub. Date: Nov. 3, 2011

(65) Prior Publication Data
US 2013/0138064 A1    May 30, 2013

(30) Foreign Application Priority Data

Apr. 29, 2010  (DK) .................................. 2010 70180

(51) Int. Cl.
*A61F 5/443*    (2006.01)
*A61F 5/442*    (2006.01)
*A61F 5/445*    (2006.01)
*A61F 5/448*    (2006.01)
(Continued)

(52) U.S. Cl.
CPC ....... *A61F 5/443* (2013.01); *A61F 2013/00974* (2013.01); *A61F 2013/00978* (2013.01); *A61F 15/02* (2013.01); *A61F 5/442* (2013.01); *A61F 5/445* (2013.01); *A61F 5/448* (2013.01); *A61M 16/047* (2013.01)

(58) Field of Classification Search
CPC .. A61B 2019/461; A61B 5/107; A61B 5/445; A61B 5/684; A61F 13/02; A61F 13/0269; A61F 15/02; A61F 2013/00974; A61F 5/442; A61F 5/443; A61F 5/445; A61F 5/448; A61F 2013/00851; A61F 2013/00182; A61F 2013/00553; A61F 1/0088; A61F 2013/00536; A61F 2013/0054; A61F 13/00068; A61F 13/00085; A61F 13/023; A61F 2013/00978; A61M 16/047; A61M 1/0088
See application file for complete search history.

(56) References Cited

U.S. PATENT DOCUMENTS 3,837,342 A  *  9/1974  Mitsuo ......................... 604/344
3,941,133 A     3/1976  Chen
(Continued)

FOREIGN PATENT DOCUMENTS

WO           9853771        12/1998
WO    WO 2011123018 A1  *  10/2011

*Primary Examiner* — Adam Marcetich
(74) *Attorney, Agent, or Firm* — Coloplast Corp., Coloplast A/S; Nick Baumann

(57) ABSTRACT

The present invention relates to a kit comprising at least one base plate for adhesive attachment to the skin around at least one body opening. The kit further comprises at least one separate peripheral device for attachment to the base plate. The base plate comprises a backing layer, having a proximal side facing the user during use, where a skin friendly adhesive is disposed on said proximal side of the backing layer and wherein the base plate is an intact base plate thereby allowing a hole to be cut at a desired position before use. The separate peripheral device comprises a continuous adhesive ring for permanent adhesive attachment between the continuous adhesive ring of the peripheral device and the distal side of the backing layer of the base plate. This allows the user to provide a custom fit for irregular body openings.

8 Claims, 2 Drawing Sheets

(51) Int. Cl.
    *A61F 13/00*        (2006.01)
    *A61F 15/02*        (2006.01)
    *A61M 16/04*        (2006.01)

(56) References Cited

U.S. PATENT DOCUMENTS

| | | | | |
|---|---|---|---|---|
| 4,681,574 | A * | 7/1987 | Eastman | 604/344 |
| 4,890,608 | A | 1/1990 | Steer | |
| 5,079,843 | A * | 1/1992 | Shelton et al. | 30/310 |
| 5,236,426 | A * | 8/1993 | Schottes et al. | 604/334 |
| 5,265,605 | A * | 11/1993 | Afflerbach | 600/300 |
| 5,738,661 | A * | 4/1998 | Larice | 604/180 |
| 6,659,989 | B1 * | 12/2003 | Otto | 604/344 |
| 6,823,764 | B1 * | 11/2004 | Tsubota | 83/249 |
| 2004/0054339 | A1 * | 3/2004 | Ciok et al. | 604/334 |
| 2004/0111072 | A1 | 6/2004 | McKissick | |
| 2005/0177119 | A1 * | 8/2005 | Tsai | 604/332 |
| 2006/0079852 | A1 * | 4/2006 | Bubb et al. | 604/317 |
| 2006/0293630 | A1 * | 12/2006 | Manna et al. | 604/327 |
| 2007/0282271 | A1 * | 12/2007 | Kaplan et al. | 604/174 |
| 2008/0287892 | A1 * | 11/2008 | Khan et al. | 604/313 |
| 2009/0234313 | A1 * | 9/2009 | Mullejeans et al. | 604/338 |
| 2009/0264805 | A1 * | 10/2009 | Davis et al. | 602/43 |
| 2009/0306580 | A1 * | 12/2009 | Blott et al. | 604/22 |
| 2010/0016815 | A1 * | 1/2010 | Vitaris et al. | 604/304 |
| 2010/0022975 | A1 | 1/2010 | Bosch | |
| 2010/0057025 | A1 * | 3/2010 | Aicher | 604/319 |
| 2010/0145293 | A1 * | 6/2010 | Verhaalen | 604/337 |
| 2011/0196278 | A1 * | 8/2011 | Svedman et al. | 602/43 |
| 2011/0213322 | A1 * | 9/2011 | Cramer et al. | 604/344 |
| 2011/0218508 | A1 * | 9/2011 | Cason | 604/342 |
| 2012/0029450 | A1 * | 2/2012 | Grum-Schwensen | 604/344 |

* cited by examiner

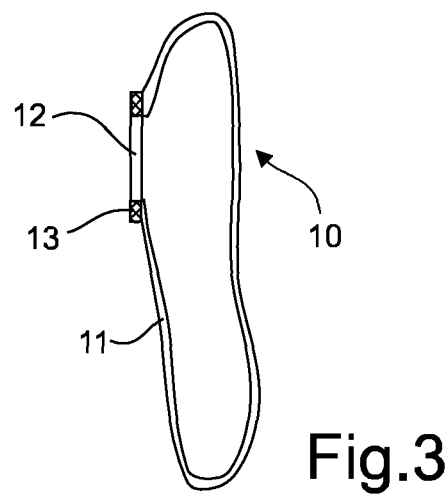
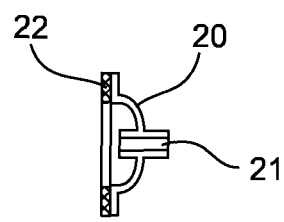 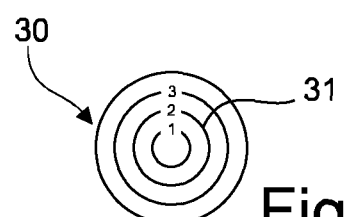

CUSTOMIZABLE COLLECTION DEVICE

TECHNICAL FIELD

The present invention relates to a kit comprising a base plate and at least one peripheral device, such as a collecting bag, for providing a customized collection device for a body opening. The kit may comprise further elements for even better customization.

BACKGROUND

Today there is a wide range of ostomy bags for ostomates, i.e. persons having a stoma, for collecting output from the stoma. However, a stoma is very individual from person to person. It may for example be the size of the stoma, whether it is a sunken stoma or protruding stoma or something in between. The peristomal area (the skin area surrounding the stoma) varies significantly, and additionally many ostomates also get fistulas, i.e. body generated openings around the stoma. All these factors and more make it difficult to make the perfect product for an ostomate, and although there already is a wide range of products many ostomates are not able to find a product suitable for their stoma.

This has lead to what is referred to as 'plumbing', i.e. that ostomates acquire different products and subsequently modify them to fit their need. In many ways, this is inconvenient, as plumbing leads to solutions which leaks or fall apart. Furthermore, this is both expensive and time consuming for the ostomates as he has to buy different products and combine them in order to obtain a satisfactory solution while spending time on cutting and assembling the constructions.

Thus, there is a need for providing an alternative for those ostomates where standard ostomy appliances does not fit and where such an alternative may be modified with a minimum of work to suit that ostomate's stoma while still providing relatively high security against leakage compared to typical plumbing solutions.

Such an alternative could preferably also be used for other users than ostomates, e.g. people who have had removed excess skin and have a temporary wound area that needs to be covered and protected while healing.

BRIEF DESCRIPTION

The present invention relates to a kit comprising at least one base plate for adhesive attachment to the skin around at least one body opening and at least one separate peripheral device for attachment to the base plate, wherein
  the base plate comprises a backing layer, having a proximal side facing the user during use, where a skin friendly adhesive is disposed on said proximal side of the backing layer and wherein the base plate is an intact base plate thereby allowing a hole to be cut at a desired position before use, and
  the separate peripheral device comprises a continuous adhesive ring for permanent adhesive attachment between the continuous adhesive ring of the peripheral device and the distal side of the backing layer of the base plate.

In most base plates for use with for example ostomy collecting bags, the base plate is provided with a pre-cut hole, thereby facilitating cutting of the through-going hole to fit the stoma. However, by providing a base plate having no pre-cut hole, it is possible to allow the user to cut or punch out one or more holes at any location on the base plate. Thus, the term 'intact' as used herein should be understood as being a base plate wherein no pre-cut holes are provided.

By attaching the peripheral device directly to the backing layer of the base plate, it is possible to cut one or more holes in the base plate that are in alignment with respective body openings, i.e. folds, scars, wound sites, stomas or fistulas. This allows the user to achieve a custom fit for irregular body openings while reducing the risk of leakage and reduce the time for application of the base plate and collecting bag.

Seeing that the peripheral device is attached directly to the base plate, the adhesive attachment has to be able to follow the curvature and movement of the body without detaching, as this would result in leakage or even spillage of stomal output. Thus, it is important that the adhesive attachment is permanent, or in other words that when the adhesive attachment has been established then the peripheral device cannot be removed without either tearing the base plate or the peripheral device or detaching the base plate from the skin.

In order to prevent the peripheral device to unintentionally adhere to its surroundings the continuous adhesive ring may advantageously be covered by a release layer which is removable before establishing the permanent adhesive attachment.

In one embodiment, at least the distal side of the backing layer is plane. This provides a large contact surface with the peripheral device whereby a high adhesive attachment can easily be obtained.

A kit as disclosed herein can be used with a number of different body openings, for example stomas such as colostomies, ileostomies, urostomies or tracheostomies. Other body openings could be fistulas, chronic wounds and/or ulcers.

In one embodiment, the at least one peripheral device is a collecting bag comprising an inlet opening for receiving output from said body opening, where a continuous adhesive ring is arranged surrounding said inlet opening for adhesive attachment between the adhesive ring and the backing layer of the base plate.

This provides a solution where the collecting bag can be easily attached to a base plate having at least one customized hole placed according to the user preference.

To further facilitate the application of the base plate and the collecting bag, the kit may further comprise at least one marker to be attached to the base plate for indicating where a hole is to be cut. In one embodiment, such marker could be a transparent plastic sheet whereon cutting indications are arranged.

In some embodiments, the at least one peripheral device can be a drainage port having a continuous adhesive ring for adhesive attachment of the drainage port to the backing layer of the base plate. This is for example advantageous to users who besides for example a stoma also have a fistula or peristomal wound to which access is desirable for cleaning or draining fluid or other treatment.

In yet an alternative or additional embodiment, a hole may be cut in the ostomy bag whereon the drainage port is attached.

In some situations, the user may need to customize a two-piece ostomy solution, where the collecting bag or other peripheral devices need to be replaced without also changing the base plate.

Such embodiment, may for example comprise the at least one peripheral device being a flexible flange in the form of a flexible disc having a through-going disc hole wherein a continuous adhesive ring is arranged on the proximal side of the flexible flange and encircles said through-going disc hole.

This would create the option of attaching an ostomy collecting bag having an adhesive attachment flange to the distal side of the flexible flange.

Alternatively, in another embodiment, the at least one peripheral device is a mechanical coupling having a distal side for coupling with a complementary coupling on an ostomy bag, said mechanical coupling having a continuous adhesive ring arranged on the proximal side. This allows the user to provide a mechanical two-piece ostomy device solution, wherein the ostomy collecting bag may be replaced via a mechanical coupling.

The invention also relates to a method of using a kit as described above, comprising the steps of
cutting at least one through-going hole in the base plate, and
attaching at least one peripheral device to the base plate around at least one of the holes so that the respective continuous adhesive ring encircles said at least one hole so that the permanent adhesive attachment is established between the continuous adhesive ring of the peripheral device and the distal side of the backing layer of the base plate.

Typically, the number of holes corresponds to the number of body openings the base plate will cover. However, one hole can also encircle two or more body openings. Moreover, one peripheral device will typically cover one hole in the base plate. However, a peripheral device such as a collecting bag can be connected to two or more holes.

Preferably, the method further comprises the step of subsequently attaching the base plate to the skin of a user after the peripheral devices has been attached to the base plate. This allows a more secure application, since the attachment can be performed on a plane surface, e.g. a table, than if the base plate is first applied to the skin of the user and subsequently the at least one peripheral device is attached to the base plate, since in this case the attachment will be more difficult as care must be taken to follow the curves and folds of the skin in order to prevent leaks.

As can be understood, a plurality of peripheral devices may be envisioned to be used with the kit as claimed herein. Furthermore, the kit is not limited to one kind of peripheral device but different types of peripheral devices may be used in the kit in order to solve the need of the specific user.

BRIEF DESCRIPTION OF THE DRAWINGS

FIG. 3 shows in section a collection bag for use with a base plate as described in FIGS. 1 and 2,
FIG. 4 shows in section a drainage port for use with a base plate as described in FIGS. 1 and 2,
and
FIG. 5 shows a marker for indicating a cutting site on the base plate.

DETAILED DESCRIPTION

Figure 1:
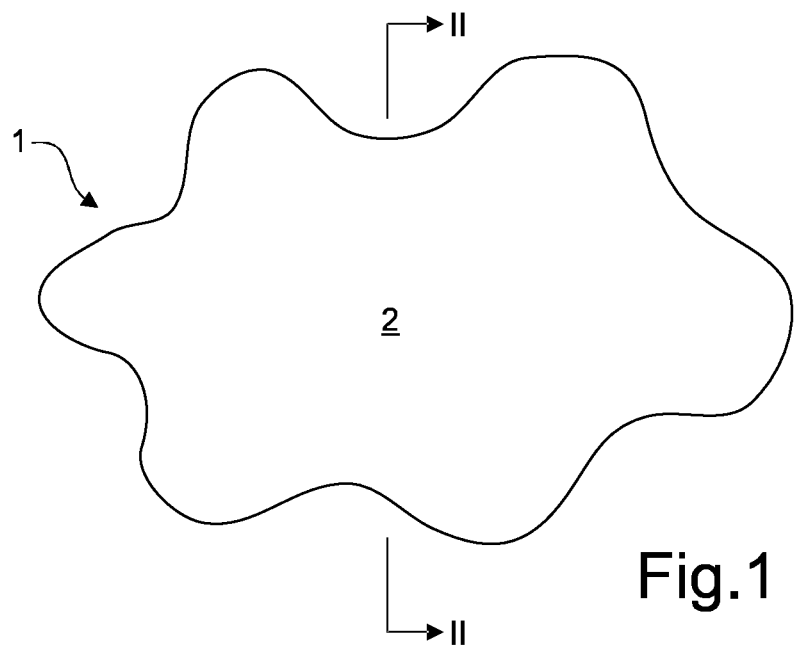
FIG. 1 shows from the distal side an embodiment of a base plate as described herein.
Figure 2:
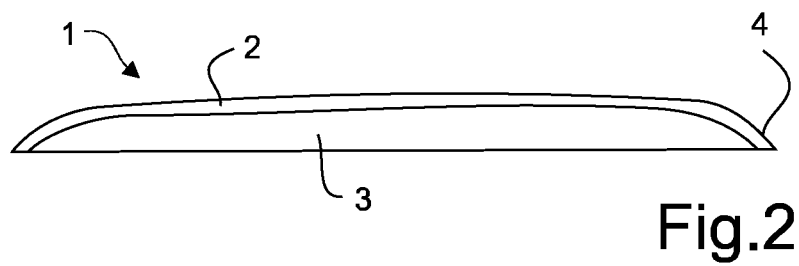
FIG. 2 shows the above in section along lines II-II.

FIGS. 1 and 2 show one embodiment of a base plate 1. The base plate is formed of a backing layer 2 whereon a skin friendly adhesive 3 is disposed on the proximal side, which is the side that will face the user during wear. Along the edge, the base plate is formed with a curved or bevelled finish 4 so that no adhesive is exposed to the surroundings when the base plate is worn. This prevents the base plate from sticking to clothing and other articles which may unintentionally detach the base plate.

As shown in FIG. 1, the base plate has a curved, flower-like shape. However, the base plate may have any shape. Furthermore, the backing layer and the skin friendly adhesive extend completely across the area defined by the periphery of the base plate, thereby providing no pre-formed holes.

A collecting bag 10 for use with the base plate as described above is shown in FIG. 3. The collecting bag is formed of a bag foil 11 having an opening 12 through which output from a body opening can enter. The collecting bag may also be formed of two flexible plastic films which are welded together along their periphery. Surrounding the opening, there is a first adhesive ring 13 which is suited for adhesive connection with the backing layer of the base plate. The first adhesive ring is continuous, thereby providing a tight seal that reduces the risk of leakage.

A drainage port 20 for use with the base plate is shown in FIG. 4. The drainage port has an access opening 21 allowing access to the body opening, for e.g. cleaning or treatment. A second adhesive ring 22 is provided around the access opening and allows the drainage port to be adhesively attached to the backing layer of the base plate.

A marker 30 for indicating a cutting location is shown in FIG. 5, The marker is in the form of a transparent plastic disc. On one side, an adhesive is disposed which allows the marker to be adhesively attached to the backing layer of the base plate. A cutting guide 31 is printed on the surface. In the current embodiment, the cutting guide is in the form of three concentric circles, one being one centimeter in diameter, a second being two centimeters in diameter and a third being three centimeters in diameter.

By providing an ostomate with a kit having one or more of the above parts, he will be able to provide a solution for his personal need. Typically, this will be achieved by holding the base plate up in alignment with the stoma and marking the stoma by placing a marker on the backing layer. Other markers may also be placed to mark e.g. a fistula or other wound site. Then through-going holes are cut at the markers location. The first number of times this is done the user may have to cut carefully and often compare to see if the sizes and location of the markers match the area to be bandaged. However, after some time, practice will allow the user to know which size and shape of holes has to be cut at the markers.

After the holes are cut the appropriate number of the collecting bags and drainage ports are attached to the backing layer around each hole and the base plate is subsequently attached to the skin at the body opening.

In order to provide optimal attachment between the backing layer and the peripheral device, it has been found that the backing layer should preferably be formed of polyurethane. Most of the suitable adhesives will adhere so well to polyurethane that an attempt to separate the peripheral device from the base plate will be impossible without tearing the assembly.

Moreover, the skin friendly adhesive should be of a kind which is suitable for a lot of skin types and which is flexible, easy to cut and easy to mould. Such skin friendly adhesives are described in for example EP 0 938 349 B1 and WO 2007/076862 A1. In particular, a layered adhesive construction comprising a first and a second layer of hydrocolloid adhesive having different compositions, where the second layer of hydrocolloid adhesive is interposed between the first layer of hydrocolloid adhesive and a backing layer, wherein the first adhesive layer is a layer of mouldable adhesive comprising hydrocolloids having a Strain Recovery below 45% when measured as described in WO 2007/076862 A1 and the second adhesive layer is a layer of hydrocolloid adhesive having a Strain Recovery above 55% when measured as described in WO 2007/076862 A1, is suitable for use in the kit as described herein. Specifically Examples 1-3 in WO 2007/076862 A1 are examples well suited to be used in the kit.

The invention claimed is:

1. A method for handling bodily effluents from a patient, wherein the handling comprises the steps of:
   manufacturing an intact base plate having an absence of a hole within an outermost perimeter of the intact base plate, the base plate comprising a backing layer having a proximal side and a distal side, the proximal side comprising a continuous adhesive for attachment to a skin surface of the patient, wherein the continuous adhesive prevents leaks to an external environment of the base plate;
   cutting a first through-going hole in the base plate, the first through-going hole sized to correspond to a first body opening on the skin surface;
   cutting a second through-going hole in the base plated spaced a distance away from a periphery of the first through-going hole, the second through-going hole sized to correspond to a second body opening on the skin surface;
   attaching a first peripheral device to the distal side of the backing layer of the base plate around the first through-going hole;
   attaching a second peripheral device separate from the first peripheral device to the distal side of the backing layer of the base plate around the second through-going hole; and
   configuring the proximal side of the base plate for attachment to the skin surface of the user such that each of the first and second through-going holes locates over a respective one of the first body opening and the second body opening and configuring each of the first and second separate peripheral devices to receive bodily effluent from each of the first and second body opening respectively.

2. The method according to claim 1, comprising attaching a first marker to the base plate to indicate a position of the first hole before cutting the first through-going hole in the base plate.

3. The method according to claim 2, comprising attaching a second marker to the base plate to indicate a position of the second hole before cutting the second through-going hole in the base plate.

4. The method according to claim 2 or 3, wherein each of the first and second markers comprises a transparent plastic sheet with cutting indicators.

5. The method according to claim 1, comprising attaching a continuous adhesive ring of each of the first and second separate peripheral devices around each of the first and second through-going holes for permanent adhesive attachment of the continuous adhesive ring of the respective peripheral device to the distal side of the backing layer of the base plate.

6. The method according to claim 1, wherein the first separate peripheral device is a collecting bag comprising an inlet opening for receiving output from the first body opening and the second separate peripheral device is a drainage port for access to the second body opening.

7. The method according to claim 1, wherein at least one of the first and second separate peripheral devices comprises a first coupling half provided on a distal surface of the peripheral device and configured for coupling to second coupling half provided around an inlet opening of a collection bag for bodily effluents.

8. The method according to claim 1, further comprising cutting one or more additional through-going holes in the base plate spaced from the first and second through-going holes.

* * * * *